US00RE39238E

(19) United States
(12) Reissued Patent
Logemann et al.

(10) Patent Number: US RE39,238 E
(45) Date of Reissued Patent: Aug. 15, 2006

(54) TRANSGENIC PATHOGEN-RESISTANT ORGANISM

(75) Inventors: Jürgen Logemann, Schillestadt (DE); Guido Jach, Cologne (DE); Birgit Görnhardt, Köln (DE); John Mundy, Copenhagen (DK); Jeff Schell, Köln (DE); Peter Eckes, Kelkheim (DE); Ilan Chet, Nes Ziona (IL)

(73) Assignee: Max-Planck-Gesellschaft zür Forderung der Wissenschaften e.V., Gottingen (DE)

(21) Appl. No.: 09/729,141

(22) Filed: Dec. 1, 2000

Related U.S. Patent Documents

Reissue of:
(64) Patent No.: 5,804,184
Issued: Sep. 8, 1998
Appl. No.: 08/812,025
Filed: Mar. 6, 1997

U.S. Applications:
(62) Division of application No. 08/457,797, filed on Jun. 1, 1995, now Pat. No. 5,689,045, which is a continuation of application No. 08/134,416, filed on Oct. 8, 1993, now abandoned.

(30) Foreign Application Priority Data

Oct. 9, 1992 (DE) ..... P42 34 131

(51) Int. Cl.
*A61K 38/54* (2006.01)
*A61K 38/47* (2006.01)
*A61K 38/16* (2006.01)

(52) U.S. Cl. ..... 424/94.61; 424/94.2; 514/12; 435/200; 435/209

(58) Field of Classification Search ..... 435/252.3, 435/419, 209, 320.1, 200; 424/94.61, 94.2; 514/12
See application file for complete search history.

(56) References Cited

U.S. PATENT DOCUMENTS 4,940,840 A * 7/1990 Suslow et al. ..... 800/205
4,970,168 A 11/1990 Tumer ..... 435/317.1

FOREIGN PATENT DOCUMENTS

| | | | |
|---|---|---|---|
| DE | 3810286 | | 3/1988 |
| DE | 4040954 | | 12/1990 |
| EP | 440 304 | * | 8/1991 |
| EP | 440304 | | 8/1991 |
| WO | 8904371 | | 5/1989 |
| WO | 9119738 | | 12/1991 |
| WO | 9216632 | | 10/1992 |
| WO | 9217591 | | 10/1992 |
| WO | 9408009 | | 4/1994 |

OTHER PUBLICATIONS

R. Leah et al., "Biochemical and Molecular Characterization of Three Barley Seed Proteins With Antifungal Properties", J. Biol. Chem. 266(3): 1564–1573, Jan. 1991.*
S. Wnendt et al., "Cloning and Nucleotide Sequences of a cDNA Encoding the Antifungal–Protein of *Aspergillus giganteus* and Preliminary Characterization of the Native Gene", Nuc. Acid Res. 18(13): 3987, Jul. 1990.*
Dunsmuir et al., Curr. Pl. Sci. and BioTech. in Agri., vol. 14, Adv. in Mol. Gen. of Plant–Microbe Interactions, Seattle Wash., Jul. 1992, Kluwer Acad. Publ. Netherlands, pp. 567–571.
Bojsen et al., 1992, Dev. Plant Pathol. 2 (Mech. of Pl. Def. Res.) Symposium held Aug. 24–27, pp. 449.
Jach et al., 1992, Bio/Technol. 1:33–40.
Logemann et al., 1992, Bio/Technol. 10:305–308.
Broglie et al., 1991, Science 254:1194–1197.
Potrykus, 1990, Bio/Technology 8:535–542.
Leah and Mundy, 1989, Plant Molecular Biol. 12:673–682.
Topfer et al., 1987, Nucl. Acids Res. 15:5890.
Hahlbrock and Grisebach, 1979, Ann. Rev. Plant. Physiol. 30:105–130.
Boller, 1985, Cellular and Molecular Biology of Plant Stress, UCLA Symp. Mol. Cell. Biol. New Ser. 22:247–262.
R. Leah et al., "Biochemical and Molecular Characterization of Three Barley Seed Proteins With Antifungal Properties", J. Bio. Chem (266(3); 1564–1573, Jan. 1991.
S. Wnendt et al., "Cloning and Nucleotide Sequences of a cDNA Encoding the Antifungal–Protein of *Aspergillus giganteus* and Preliminary Characterization of the Native Gene", Nuc. Acid Res. 18(13): 3987, Jul. 1990.

* cited by examiner

*Primary Examiner*—Rebecca E. Prouty
(74) *Attorney, Agent, or Firm*—Baker Botts LLP

(57) ABSTRACT

Transgenic pathogen-resistant organism whose genome contains at least two different genes under the control of active promoters with pathogen-inhibiting action. This organism is distinguished by a synergistic pathogen-inhibiting action. This action is evident particularly when the genes code for the gene products chitinase (ChiS, ChiG), glucanase (GluG), protein synthesis inhibitor (PSI) and antifungal protein (AFP).

2 Claims, 2 Drawing Sheets

TRANSGENIC PATHOGEN-RESISTANT ORGANISM

Matter enclosed in heavy brackets [ ] appears in the original patent but forms no part of this reissue specification; matter printed in italics indicates the additions made by reissue.

[This is a divisional of application No. 08/457,797, filed on Jun. 1, 1995, now U.S. Pat. No. 5,689,045, which is a continuation of Ser. No. 08/134,416, filed on Oct. 8, 1993, now abandoned.] *The present application is a reissue of application Ser. No. 08/812,025, filed Mar. 6, 1997, which issued as U.S. Pat. No. 5,804,184, which is a divisional of application Ser. No. 08/457,797, filed Jun. 1, 1995, which issued as U.S. Pat. No. 5,689,045 and which is now reissue application Ser. No. 09/729,141 which is a continuation of application Ser. No. 08/134,416, filed on Oct. 8, 1993, now abandoned.*

FIELD OF THE INVENTION

The invention relates to a pathogen-resistant organism and to a process for generating it.

BACKGROUND OF THE INVENTION

It is known in the state of the art that infestations of a plant by pathogens causes a series of different reactions. These include, for example, changes in the cell wall structure, the synthesis of phytoalexins which have antimicrobial activity, the accumulation of so-called PR proteins (pathogenesis-related), protease inhibitors and enzymes with hydrolytic functions (Hahlbrock and Grisebach in Ann. Rev. Plant. Physiol., 30 (1979), 105–130).

Many pathogens (fungi and insects) have chitin as a constituent of their cell wall. By contrast, plants posses no chitin. It has now been demonstrated in some cases that there is enhanced production of chitinases in plants after infestation by pathogens. Chitinases are among the enzymes with hydrolytic functions and they catalyze chitin breakdown. It has now been possible to show that plants acquire an increased resistance to pathogens by the production of chitinases.

It is furthermore known to use a gene from barley plants whose gene product codes for an inhibitor of fungal protein synthesis. The incorporation of a corresponding inhibitor gene in transgenic plants led to improved resistance to fungi.

Finally, it has also been disclosed that the use of a polypeptide from Aspergillus giganteus is able to protect, by virtue of its antifungal activity, plants from infestation by fungi.

However, given this state of the art there is a need to provide further transgenic pathogen-resistant organisms. Moreover, the organisms which are particularly desired are those whose resistance is increased overall by comparison with the known organisms or is extended with respect to the number of possible pathogens.

This problem is solved by a transgenic pathogen-resistant organism having the features of the present invention.

The invention is based on the surprising finding that the incorporation of at least two different genes with pathogen-inhibiting action into the genome of an organism assists the latter to resist pathogens to an extent going far beyond an additive effect of each of the genes on its own.

The dependent claims indicate further embodiments of the invention.

The genes can code for gene products which reduce the vitality of fungi. In particular, the genes can be of fungal, bacterial and plant, animal or viral origin. In particular, the gene products have properties which promote resistance to fungi. The gene products are chitinase (ChiS, ChiG), glucanase (GluG), protein synthesis inhibitor (PSI) and antifungal protein (AFP).

The transgenic pathogen-resistant organism can be a plant, and tobacco, potato, strawberry, corn, rape or tomato plants are preferred.

The invention also relates to DNA-transfer vectors with inserted DNA sequences as are indicated in detail in this description.

The invention furthermore relates to a process for the generation of pathogen-resistant organisms as are described herein, wherein at least 1 gene with pathogen-inhibiting action is transferred into the genome of an organism, and the pathogen-resistant organism is obtained.

(a) by crossing the organism with another, optionally transgenic, organism which contains at least one other gene with pathogen-inhibiting action, and subsequently selecting, and/or (b) by transformation of this other gene with pathogen-inhibiting action into the organism. The process can be used with DNA-transfer vectors with inserted DNA sequences corresponding to a gene with pathogen-inhibiting action as described herein.

Finally, the invention relates to a process for the generation of pathogen-resistant organisms, wherein vectors which comprise more than one gene with pathogen-inhibiting action are used for the transformation into the genome of an organism.

The invention also relates to a process for ensuring the resistance of organisms to pathogens, characterized in that the organism used is a transgenic pathogen-resistant organism according to the present invention or an organism whose genome contains at least one gene complying with the definitions used herein, and at least one substance which is not expressed by the organism but corresponds to any other one of the gene products complying with the definitions given in this application is applied to the organism.

It was possible to achieve the synergistic effects very particularly with transgenic pathogen-resistant organisms to which the gene sequences which coded for proteins of the attached sequence listings A to E, or corresponded to the latter, were transferred or transfected.

ChiS:

A DNA fragment which is 1.8 Kb in size, that codes for a chitinase called ChiS (SEQ ID NO: 8) was isolated from the soil bacterium Serratia marcescens. In vitro investigations with purified ChiS protein showed that it is able effectively to inhibit the growth of fungi, even in low concentrations. The reason for the inhibition is that the ChiS protein has a chitinase activity which is able to damage the tips of the fungi hyphae. In this way the fungus is unable to grow further and is inhibited.

PSI:

The PSI gene originates from barley and codes for a protein which inhibits protein synthesis by fungi. In vitro tests show that even low concentrations of PSI are sufficient to inhibit various fungi such as, for example, Rhizoctonia solani.

AFP:

It is possible for a polypeptide which has antifungal activity to be isolated from the fermentation broth of Aspergillus giganteus and to be sequenced. This polypeptide is suitable as antifungal agent, for example as spraying agent and as preservative for industrial products and human and animal foods. It can furthermore be combined with other substances which have pesticidal activity, fertilizers or growth regulators. Inhibitory activities against fungi were detectable inter alia against various Aspergillus, Fusaria, Phytophthora and Trichophyton species.

ChiG and GluG:

Two genes which code, respectively, for a chitinase (ChiG) and glucanase (GluG) can be isolated from certain types of barley. Purified ChiG protein or GluG protein inhibits various phytopathogenic fungi in vitro (inter alia Rhizoctonia solani) (see R. Leah et al., Journal of Biological Chemistry, Vol. 266, No. 3 (1991), pages 1564–1573).

SUMMARY OF THE INVENTION

The inventors have now found, completely surprisingly, that an at least binary combination of expression of PSI, AFP, ChiS, ChiG or GluG leads to synergistic effects in respect of the acquired resistance to fungi in transgenic plants. In particular, the effects of the individual substances in the combination are markedly exceeded. These include resistance to the fungus Rhizoctonia solani, Sclerotinia infestation, Botrytis infestation, etc.

Combinations according to the invention are (DNA and/or polypeptides):

(binary combinations)

ChiS, GluG; ChiS, PSI; ChiS, ChiG; ChiS, AFP; GluG, PSI; GluG, ChiG; GluG, AFP; PSI; ChiG; PSI, AFP; (ternary combinations)

ChiS, GluG, PSI; ChiS, GluG, ChiG; ChiS, GluG, AFP; GluG, PSI, ChiG; GluG, PSI, AFP; PSI, ChiG, AFP; ChiG, AFP, GluG (quaternary combinations)

ChiS, GluG, PSI, AFP; ChiS, GluG, PSI, ChiG; (quinary combination)

ChiS, GluG, PSI, AFP, ChiG

The invention furthermore relates to the combined use of the proteins with pathogen-inhibiting action, preferably ChiS, PSI, AFP, ChiG and GluG, against pathogens. Combined use also means in this context that at least a first pathogen-inhibiting substance is expressed by the organism and at least a second substance which has pathogen-inhibiting action is applied to the organism from outside.

The agents according to the invention also include those which contain the abovementioned proteins in at least binary combination. The agents according to the invention can contain other active substances besides the proteins. The other active substances can be pesticides, fertilizers and/or growth regulators, and the agents according to the invention can be prepared in various formulations such as concentrates, emulsions, powders, formulations or carriers, mixtures with other active substances, etc. The ChiS/PSI and AFP/PSI combination is particularly preferred. These proteins can be used particularly effectively to inhibit the growth of Rhizoctonia solani, especially in tobacco crops.

DETAILED DESCRIPTION OF THE INVENTION

Figure 1:
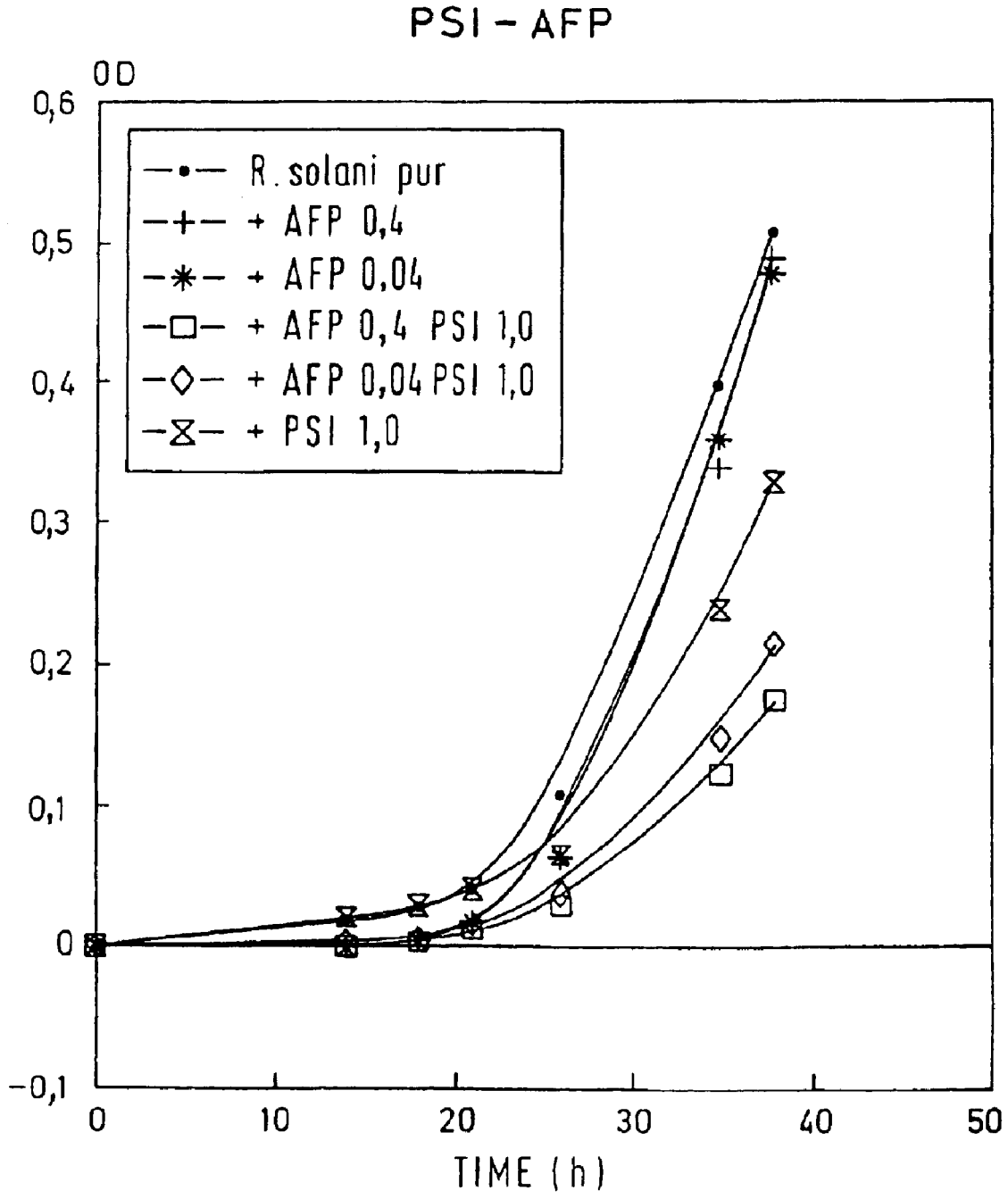
FIG. 1 shows the effects of AFP and PSI on Rhizoctonia solani.

The invention also relates to the use in a process according to the invention of a DNA sequence which codes at least for a polypeptide of sequences A to E, in which sequence A is the sequence of a 60 amino acid AFP protein (SEQ ID NO: 2); sequence A' is the sequence of 51 amino acid AFP protein (SEQ ID NO: 3); sequence B is the sequence of the PSI protein (SEQ ID NO: 5); sequence B' is the sequence of a protein encoded by an incomplete PSI-cDNA clone (SEQ ID NO: 7); sequence D is the sequence of the ChiG protein (SEQ ID NO: 10); and sequence E is the sequence of the GluG protein (SEQ ID NO: 12) or to a pathogen-resistant organism, where its genome contains at least two different genes under the control of active promoters with pathogen-inhibiting action, where the genes are in each case selected from the group of sequences A to E, in which sequence A is the sequence of a nucleic acid (SEQ ID NO: 1) which comprises a region encoding AFP protein; sequence B is the sequence of a nucleic acid (SEQ ID NO: 4) which comprises a region encoding PSI protein; sequence B' is the sequence of a nucleic acid (SEQ ID NO: 6) which was identified as a portion of an incomplete PSI-cDNA clone; sequence C is the sequence of a nucleic acid (SEQ ID NO: 8) encoding ChiS protein; sequence D is the sequence of a nucleic acid (SEQ ID NO: 9) which comprises a region encoding ChiG protein; and sequence E is the sequence of a nucleic acid (SEQ ID NO: 11) which comprises a region encoding GluG protein. The invention furthermore includes DNA sequences which hybridize with a DNA sequence which codes for polypeptides of amino-acid sequences A to E, in which sequence A is the sequence of a 60 amino acid AFP protein (SEQ ID NO: 2); sequence A' is the sequence of a 51 amino acid AFP protein (SEQ ID NO: 3); sequence B is the sequence of the PSI protein (SEQ ID NO: 5); sequence B' is the sequence of a protein encoded by an incomplete PSI-cDNA clone (SEQ ID NO: 7); sequence D is the sequence of the ChiG protein (SEQ ID NO: 10); and sequence E is the sequence of the GluG protein (SEQ ID NO: 12), where these DNA sequences can be of natural, synthetic or semisynthetic origin and can be related to the abovementioned DNA sequence by mutations, nucleotide substitutions, nucleotide deletions, nucleotide insertions and inversions of nucleotide sequences, and for a polypeptide with pathogenic activity. The invention furthermore relates to a recombinant DNA molecule which contains at least one DNA sequence which accords with the preceding statements, where this DNA molecule can be in the form of a cloning or expression vector.

The invention relates to appropriate host organisms and intermediate hosts which are transformed with a recombinant DNA molecule which accords with the preceding statements. Preferred as intermediate host in the generation of a pathogen-resistant transgenic organism are strains of bacteria, in particular so-called Agrobacteria strains.

The invention furthermore relates to the transgenic pathogen-resistant organisms obtained by the process according to the invention, in particular tobacco, potato, corn, pea, rape and tomato plants.

The DNA sequences according to the invention are, as a rule, transferred together with a promoter. Promoter sequences are recognized by the plant transcription apparatus and thus lead to constitutive expression of the gene associated with them in plants. The promoter can, however, also be pathogen-inducible and/or wound-inducible (WUN1) and/or tissue-specific and/or development-specific.

The genetic manipulation operations necessary for carrying out the invention, especially for expression of the gene in plants, are generally known. See for example the publication by Maniatis et al. in "Molecular cloning: A laboratory manual", Cold Spring Harbor (1982).

The invention is explained in detail in the following examples.

All the standard methods of molecular biology were carried out, unless otherwise indicated, as described by Maniatis et al., "Molecular cloning: a laboratory manual", Cold Spring Harbor (1982).

The DNA (SEQ ID NO: 1; SEQ ID NO: 4; SEQ ID NO: 6; SEQ ID NO: 8; SEQ ID NO: 9; SEQ ID NO: 11) coding for amino-acid sequences A to E (SEQ ID NO: 2; SEQ ID NO: 3; SEQ ID NO: 5; SEQ ID NO: 7; SEQ ID NO: 10; SEQ ID NO: 12) was initially cloned in a manner known per se and then transferred by conjugation into A. Tumefaciens LBA 4404 (A. Hoekema et al., Nature 303, 179–180). This took place by the method described by Van Haute et al. in EMBO J. 2, 411–418 (1983).

The transfer of DNA into that Agrobacterium was checked by isolating Agrobacterium DNA by the method described by Ebert et al. in Proc. Natl. Acad. Sci. USA 84 5745–5749 (1987). Restriction cleavage of the DNA, transfer to Hybond-N membrane (Amersham) and hybridization with a radioactively labeled DNA probe provided information about successful DNA transfer into the Agrobacterium.

The transformed Agrobacterium was then used to transform tobaco, rape, strawberry, tomato and potato plants.

The LBA4404 Agrobacteria required for the infection were initially cultivated in selective antibiotic medium (P. Zambrisky et al. in EMBO J., 1, 147–152 (1983)), sedimented by centrifugation and washed in YEB medium without antibiotics (YEB=0.5% meat extract; 0.2% yeast extract; 0.5% peptone; 0.5% sucrose; 2 mM $MgSO_4$). After renewed sedimentation and taking up in $MgSO_4$ it was possible to use the bacteria for the infection.

The so-called leaf disk method was used for the infection.

Sterile leaves were used for the leaf disk infection. Leaf pieces about 1 cm in size are dipped in the previously described Agrobacteria suspension and subsequently transferred to 3 MS medium (medium described by T. Murashige and F. Skoog in Physiol. Plant., 15, 473–497 (1962); 3MS=MS−3% sucrose). After incubation at 25° C. to 27° C. with 16 hours of light for two days, the leaf pieces were transferred to MSC16 medium (according to T. Murashige (see above); MSC16=MS+0.5 μg/ml BAP+0.1 μg/ml NAA+100 μg/ml kanamycin sulfate+500 μg/ml Claforan). Shoots appearing after 4–6 weeks were cut off and transplanted to MSC15 medium (according to Murashige (see above); MSC15=MS+2% sucrose, 500 μg/ml Claforan+100 μg/ml kanamycin sulfate). Shoots with root formation were analyzed further.

Monocotyledonous plants (including corn), but some dicotyledonous plants too, were transformed by direct gene transfer into protoplasts. These protoplasts were subsequently regenerated to intact plants (Example: J. Potrykus in Biotechnology 8 (1990), 535).

The resulting transgenic plants were infected with the fungus Rhizoctonia solani for testing purposes. For this purpose, fungal cultures were grown and thoroughly mixed in standard soil. This soil was then distributed in a dish and planted with the plants to be tested.

For the evaluation, each plant on a dish was assigned a value from 0 to 3. It was possible to calculate from this for each plant line an index which resulted from the sum of the values. The classification is as follows:

0=no symptoms (healthy)

1=slightly reduced size (compared with a non-infected control); no or very slight visible infestation 2=severe reduction in growth; severe symptoms of infestation 3=dead The rating is carried out in each case 14 days after the start of the series of tests.

EXAMPLE 1:

Fungus inhibition tests with combined proteins

The invention initially was to show that the proteins used here have synergistic effects in their combination. Fungal growth tests in vitro were carried out for this purpose.

These entailed a defined amount of Rhizoctonia solani fungal mycelium being mixed with 100 μl of potato dextrose solution and incubated in microtiter plates at 25° C. In this test there is a linear correlation between the growth of the fungus and the increase in the optical density at 405 nanometers. The inhibitory effect of proteins can be detected from a smaller increase in the optical density.

2–3 mycelium balls were taken from a liquid culture of R. solani, mixed with 100 μl of KGB medium in an Eppendorf vessel and carefully homogenized with a glass mortar. This suspension was then mixed with 10 ml of KGB medium and passed through a sterile 100 μm screen. The optical density of this mycelium fragment suspension (100 μl aliquot) was adjusted to a value of 0.06–0.07 at 405 nanometers by adding medium. 100 μl samples were placed on a microtiter plate and mixed with the proteins to be tested. 7 parallels were measured per mixture. Mixtures which were mixed with the corresponding amounts of buffer served as controls. The plates were incubated in the dark at 25° C. for 48 hours, and the optical density of the cultures was measured at regular intervals.

Calculation of whether two proteins act together in an additive synergistic or antagonistic manner in the inhibition of fungal growth is possible from the measured data with the aid of the Colby formula which is described hereinafter and generally used (S. R. Colby in Wheeds, 15 (1967), 20–22).

To do this it was initially necessary to calculate the growth inhibition E to be expected theoretically with an additive behavior (the expected efficacy). This is given by:

$$E=W1+W2-((W1\times W2)/100)$$

where W1 and W2 indicate the efficacies of the individual proteins, which is defined as that percentage deviation of the growth plot (in the presence of the protein) from the untreated control. The efficacy for a protein (at a defined time in the growth plot) is given by:

$$W1=(OD(K)-OD(P))/OD(K)\times 100 \text{ (percent)}$$

In this, OD(K) is the optical density of the untreated control and OD(P) is the optical density of the culture treated with the protein.

Thus, on combined use of two proteins, the following statements were possible: if the efficacy G measured in the experiment is identical to the expected value E, the behavior is additive. If, on the other hand, G is greater than E, the behavior is synergistic.

Using this test model, it emerged that the proteins ChiS, PSI, AFP, ChiG and GluG used in the Examples surprisingly have synergistic inhibitory effects on various fungi, and these effects were achieved both by the combination of two types of proteins and by multiple combination of the above-mentioned proteins.

For example, the following values were determined from the combination of ChiS and PSI protein and from the combination of AFP protein and PSI protein on the fungus Rhizoctonia solani (in each case two different ChiS and AFP concentrations with a constant RIP concentration):

ChiS+PSI:

The expected values were: E1=29.9% and E2=44.5%

The measured values were: G1=60.4% and G2=64.1%

The proteins ChiS and PSI therefore act together in a synergistic manner in the inhibition of the growth of R. solani.

FIG. 1 shows the results obtained with the combination of the proteins and with the individual substances. According to the Figure, various ChiS concentrations (0.5 μg/ml and 0.05 μg/ml) are combined with PSi protein (1.0 μg/ml.

AFP+PSI:

The expected values were: E1=39.9% and E2=41.9%

The measured values were: G1=57.7% and G2=65.4%

Figure 2:
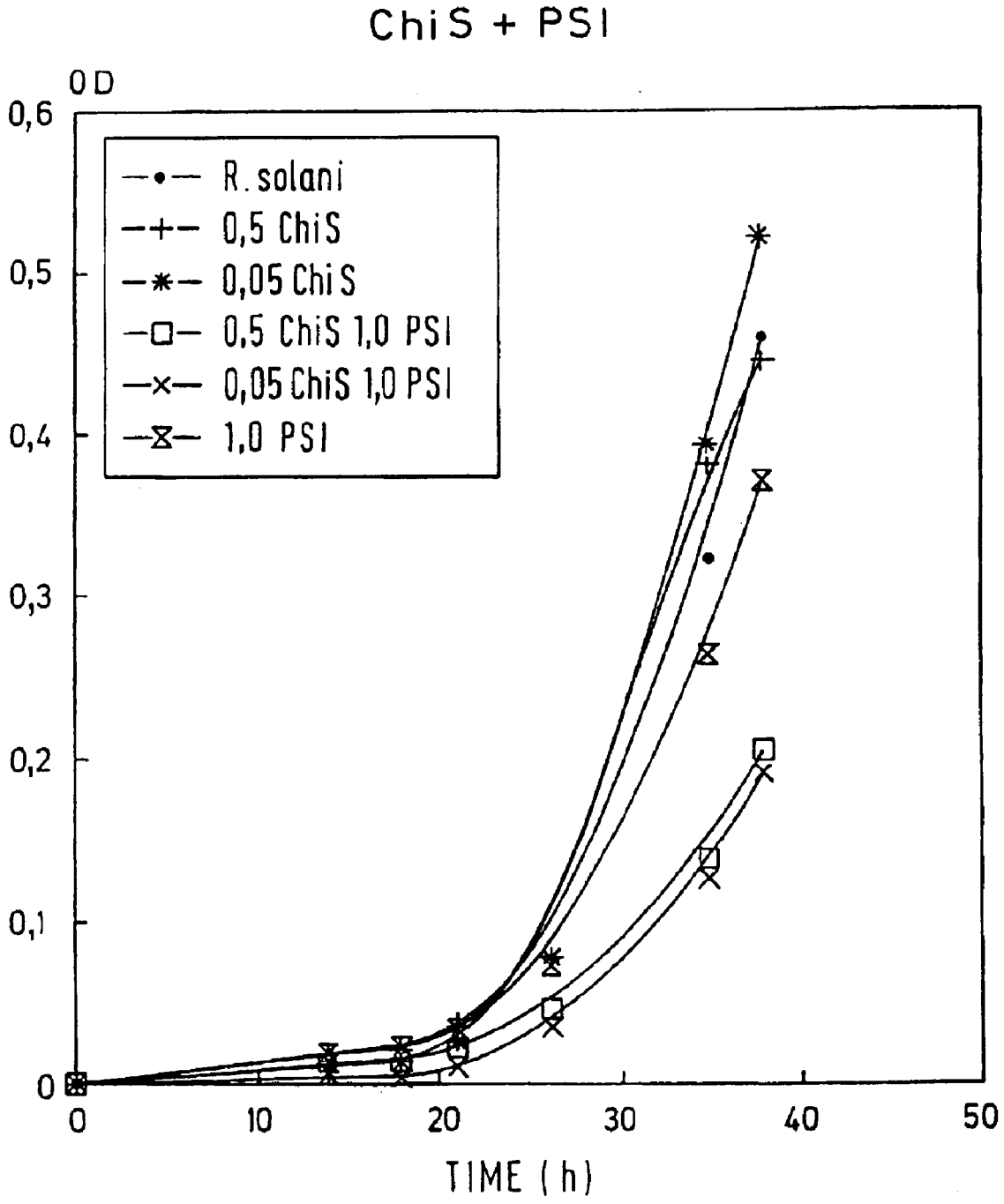
FIG. 2 shows the effects of ChiS and PSI on Rhizoctonia solani.

The AFP and PSI combination also according to this shows a synergistic inhibition of growth of the fungus R. solani. FIG. 2 indicates the test results with various AFP concentrations (0.4 μg/ml and 0.04 μg/ml) combined with PSI protein (1.0 μg/ml).

EXAMPLE 2:

Transgenic plants

In order to obtain the organisms according to the invention with DNA sequences which act together synergistically, initially transgenic plants which contained at least one of the genes which act together synergistically were generated.

ChiS in transgenic slants

Initially a ChiS gene was fused to plant regulatory sequences.

A ChiS gene 1.8 Kb in size was sequenced by using synthetic oligonucleotides in the dideoxy sequencing method of Sanger et al. in Proc. Natl. Acad. Sci. USA, 74 (1977), 5463–5467.

The 35S promoter originating from cauliflower mosaic virus (CamV) (400 bp (according to Töpfer et al. in Nucl. Acid. Res., 15 (1987), 5890)) underwent transcriptional fusion to the ChiS gene. The termination signal, which is 0.2 Kb in size, of the 35S gene of CamV, whose functionality in dicotyledonous plants is known, was used 3' from the ChiS gene. The chimeric gene 35S-ChiS was cloned into the pLS034 vector by means of the Agrobacterium tumefaciens transformation system in tobacco and potato plants, and kanamycin-resistant plants were regenerated.

It was possible to detect both the ChiS gene and the corresponding mRNA as well as the gene product protein in the resulting plants.

PSI in transgenic plants

PolyA RNA was initially isolated from ripe barley seeds (Hordeum vulgare L. cv. Piggy) and deposited in a cDNA gene bank λ-gt-11-phages. The details of the process are to be found in R. Lea in Plant. Biol., 12 (1989), 673–682. Monospecific PSI antibodies were then used to identify CDNA clones.

Subsequently, the PSI-positive λ-gt-11-phages were isolated, cloned further and sequenced by the dideoxy sequencing method of Sanger et al. indicated above. The DNA cloned into E. coli was then transferred in the manner described above by conjugation into Agrobacterium LBA4404.

Both the transferred gene and mRNA and gene product were detectable in corresponding transgenic tobacco, potato, rape, strawberry and tomato plants.

AFP in transgenic plants

For the cloning in the vector, the cDNA sequence of the antifungal peptide is provided with ends which can be ligated into BamH1 and Sal1 restriction cleavage sites. The cloning vector used was pDH51 (Pietrzak et al. in Nucl. Acids Res. 14 (1986), 5857). The vector pDH51 was opened with the restriction enzymes BamH1 and Sal1 between promoter and terminator. The vector pDH51 is a pUC18 derivative which contains promoter and terminator sequences of the 35S transcript from cauliflower mosaic virus. These sequences are recognized by the plant's transcription apparatus and lead to strong constitutive expression of the gene associated with them in plants. The DNA of the antifungal peptide is then cloned via the BamH1 and Sal1 cleavage site into the vector. Finally, the transcription unit—promoter, gene and terminator—is cut out of the vector using the restriction enzyme EcoRI and cloned into a plant transformation vector. The following vectors and their derivatives can, for example, be used as plant transformation vector:

pOCA18 (Olszewski et al. in Nucl. Acids Res., 16 (1988), 10765) pPCV310 (Koncz and Shell in MGG 204 (1986), 383) and pBin19 (Bevan et al. Nucl. Acids. Res. 12 (1984), 8711)

After the transcription unit and the vector had been ligated via the EcoRI cleavage site, the construct was conjugated into the Agrobacterium strain MP90RK (Koncz and Shell (see above)) or IHA101 (Hood et al. in J. Bacteriol. 168 (1986), 1291).

Transgenic tobacco, potato, strawberry, rape and tomato plants were then transformed by the method described above. Transformed shoots are selected on the basis of the cotransferred resistance to the antibiotic kanamycin. Expression of the antifungal protein in the transformed crop plants was checked and confirmed by DNA analysis (Southern blotting), RNA analysis (Northern blotting) and protein analysis with specific antibodies (Western blotting).

ChiG and GluG in transgenic plants

ChiG- and GluG-transgenic plants which were both Southern-, Northern- and Western-positive were obtainable in analogy to the plants described above.

ChiS, PSI, AFP, ChiG, GluG in transgenic monocotyledonous plants.

It was possible by means of direct gene transfer to integrate the abovementioned genes into the genome of monocotyledonous plants such as, for example, corn. This resulted in transgenic plants which were Southern- and Northern- and Western-positive.

Combination of various fungus-resistance genes in transgenic plants

The previously obtained tobacco, corn, rape, strawberry, potato and tomato plants were crossed together and selected for plants containing in each case the fungus-resistant genes of both parents. In addition, transgenic plants were obtained by transforming them initially with one and then with one or more other gene. Finally, plants were also transformed with vectors which contained various resistance genes. Fungus-resistance tests were done with this plant material. Surprisingly, in all cases synergistic effects, not just additive effects, in respect of fungus resistance are observed.

For example, a tobacco plant which expresses ChiS and PSI shows a considerably greater resistance to Rhizoctonia infestation than the plants which expressed only ChiS or PSI or which would result from the additive resistance.

A synergistic inhibitory effect on infestation with Rhizoctonia solani also results from combined expressed of PSI- and AFP-transgenic tobacco. Combination of two or more different genes (ChiS, RIP, AFP, ChiG and GluG) in a wide variety of transgenic plants also led to synergistic inhibitory effects on various fungi.

Whereas wild-type plants have index values from 38 to 46 in tests on 20 seedlings, it emerges with transgenic tobacco according to the invention that the latter grows as well in the presence of the fungus Rhizoctonia solani as do control plants (index value 10–12) cultivated on Rhizoctonia-free soil.

SEQUENCE LISTING

```
<160> NUMBER OF SEQ ID NOS: 12

<210> SEQ ID NO 1
<211> LENGTH: 275
<212> TYPE: DNA
<213> ORGANISM: Aspergillus giganteus
<220> FEATURE:
<221> NAME/KEY: CDS
<222> LOCATION: (46)...(225)

<400> SEQUENCE: 1

ttgccacccc cgttgaagcc gattctctca ccgctggtgg tctgg atg caa gag atg     57
                                                 Met Gln Glu Met
                                                  1

aga gcg cgg gtt ttg gcc aca tac aat ggc aaa tgc tac aag aag gat      105
Arg Ala Arg Val Leu Ala Thr Tyr Asn Gly Lys Cys Tyr Lys Lys Asp
 5                  10                  15                  20

aat atc tgc aag tac aag gca cag agc ggc aag act gcc att tgc aag      153
Asn Ile Cys Lys Tyr Lys Ala Gln Ser Gly Lys Thr Ala Ile Cys Lys
                 25                  30                  35

tgc tat gtc aaa aag tgc ccc cgc gac ggc gcg aaa tgc gag ttt gac      201
Cys Tyr Val Lys Lys Cys Pro Arg Asp Gly Ala Lys Cys Glu Phe Asp
             40                  45                  50

agc tac aag ggg aag tgc tac tgc tagacggtga gcgaagggac gaagtaggct     255
Ser Tyr Lys Gly Lys Cys Tyr Cys
         55                  60

gggggttatt ttactctgct                                                275


<210> SEQ ID NO 2
<211> LENGTH: 60
<212> TYPE: PRT
<213> ORGANISM: Aspergillus giganteus

<400> SEQUENCE: 2

Met Gln Glu Met Arg Ala Arg Val Leu Ala Thr Tyr Asn Gly Lys Cys
 1               5                  10                  15

Tyr Lys Lys Asp Asn Ile Cys Lys Tyr Lys Ala Gln Ser Gly Lys Thr
            20                  25                  30

Ala Ile Cys Lys Cys Tyr Val Lys Lys Cys Pro Arg Asp Gly Ala Lys
        35                  40                  45

Cys Glu Phe Asp Ser Tyr Lys Gly Lys Cys Tyr Cys
    50                  55                  60


<210> SEQ ID NO 3
<211> LENGTH: 51
<212> TYPE: PRT
<213> ORGANISM: Aspergillus giganteus

<400> SEQUENCE: 3

Ala Thr Tyr Asn Gly Lys Cys Tyr Lys Lys Asp Asn Ile Cys Lys Tyr
 1               5                  10                  15

Lys Ala Gln Ser Gly Lys Thr Ala Ile Cys Lys Cys Tyr Val Lys Lys
            20                  25                  30

Cys Pro Arg Asp Gly Ala Lys Cys Glu Phe Asp Ser Tyr Lys Gly Lys
        35                  40                  45
```

-continued

```
Cys Tyr Cys
    50


<210> SEQ ID NO 4
<211> LENGTH: 1032
<212> TYPE: DNA
<213> ORGANISM: Hordeum vulgare
<220> FEATURE:
<221> NAME/KEY: 5'UTR
<222> LOCATION: (1)...(42)
<220> FEATURE:
<221> NAME/KEY: CDS
<222> LOCATION: (43)...(885)
<220> FEATURE:
<221> NAME/KEY: 3'UTR
<222> LOCATION: (886)...(1032)
<223> OTHER INFORMATION: 46 nucleotides at the 3' end not shown
<220> FEATURE:
<221> NAME/KEY: polyA_signal
<222> LOCATION: (930)...(935)
<223> OTHER INFORMATION: potential polyadenylation signal
<220> FEATURE:
<221> NAME/KEY: polyA_signal
<222> LOCATION: (963)...(976)
<223> OTHER INFORMATION: potential polyadenylation signal
<220> FEATURE:
<221> NAME/KEY: polyA_signal
<222> LOCATION: (1002)...(1011)
<223> OTHER INFORMATION: potential polyadenylation signal
<220> FEATURE:
<221> NAME/KEY: mat_peptide
<222> LOCATION: (46)...(886)

<400> SEQUENCE: 4

cttaatagca catcttgtcc gtcttagctt tgcattacat cc atg gcg gca aag        54
                                               Met Ala Ala Lys
                                                1

atg gcg aag aac gtg gac aag ccg ctc ttc acc gcg acg ttc aac gtc      102
Met Ala Lys Asn Val Asp Lys Pro Leu Phe Thr Ala Thr Phe Asn Val
 5                  10                  15                  20

cag gcc agc tcc gcc gac tac gcc acc ttc atc gcc ggc atc cgc aac      150
Gln Ala Ser Ser Ala Asp Tyr Ala Thr Phe Ile Ala Gly Ile Arg Asn
                25                  30                  35

aag ctc cgc aac ccg gcg cac ttc tcc cac aac cgc ccc gtg ctg ccg      198
Lys Leu Arg Asn Pro Ala His Phe Ser His Asn Arg Pro Val Leu Pro
            40                  45                  50

ccg gtc gag ccc aac gtc ccg ccg agc agg tgg ttc cac gtc gtg ctc      246
Pro Val Glu Pro Asn Val Pro Pro Ser Arg Trp Phe His Val Val Leu
        55                  60                  65

aag gcc tcg ccg acc agc gcc ggg ctc acg ctg gcc att cgg gcg gac      294
Lys Ala Ser Pro Thr Ser Ala Gly Leu Thr Leu Ala Ile Arg Ala Asp
    70                  75                  80

aac atc tac ctg gag ggc ttc aag agc agc gac ggc acc tgg tgg gag      342
Asn Ile Tyr Leu Glu Gly Phe Lys Ser Ser Asp Gly Thr Trp Trp Glu
 85                  90                  95                 100

ctc acc ccg ggc ctc atc ccc ggc gcc acc tac gtc ggg ttc ggc ggc      390
Leu Thr Pro Gly Leu Ile Pro Gly Ala Thr Tyr Val Gly Phe Gly Gly
                105                 110                 115

acc tac cgc gac ctc ctc ggc gac acc gac aag ctg acc aac gtc gct      438
Thr Tyr Arg Asp Leu Leu Gly Asp Thr Asp Lys Leu Thr Asn Val Ala
            120                 125                 130

ctc ggc cgg cag cag ctg gcg gac gcg gtg acc gcc ctc cac ggg cgc      486
Leu Gly Arg Gln Gln Leu Ala Asp Ala Val Thr Ala Leu His Gly Arg
        135                 140                 145

acc aag gcc gac aag ccg tcc ggc ccg aag cag cag cag gcg agg gag      534
Thr Lys Ala Asp Lys Pro Ser Gly Pro Lys Gln Gln Gln Ala Arg Glu
```

-continued

```
    150                 155                 160

gcg gtg acg acg ctg ctc ctc atg gtg aac gag gcc acg cgg ttc cag      582
Ala Val Thr Thr Leu Leu Leu Met Val Asn Glu Ala Thr Arg Phe Gln
165                 170                 175                 180

acg gtg tct ggg ttc gtg gcc ggg ttg ctg cac ccc aag gcg gtg gag      630
Thr Val Ser Gly Phe Val Ala Gly Leu Leu His Pro Lys Ala Val Glu
                185                 190                 195

aag aag agc ggg aag atc ggc aat gag atg aag gcc cag gtg aac ggg      678
Lys Lys Ser Gly Lys Ile Gly Asn Glu Met Lys Ala Gln Val Asn Gly
            200                 205                 210

tgg cag gac ctg tcc gcg gcg ctg ctg aag acg gac gtg aag cct ccg      726
Trp Gln Asp Leu Ser Ala Ala Leu Leu Lys Thr Asp Val Lys Pro Pro
        215                 220                 225

ccg gga aag tcg cca gcg aag ttc gcg ccg atc gag aag atg ggc gtg      774
Pro Gly Lys Ser Pro Ala Lys Phe Ala Pro Ile Glu Lys Met Gly Val
    230                 235                 240

agg acg gct gta cag gcc gcc aac acg ctg ggg atc ctg ctg ttc gtg      822
Arg Thr Ala Val Gln Ala Ala Asn Thr Leu Gly Ile Leu Leu Phe Val
245                 250                 255                 260

gag gtg ccg ggt ggg ttg acg gtg gcc aag gcg ctg gag ctg ttc cat      870
Glu Val Pro Gly Gly Leu Thr Val Ala Lys Ala Leu Glu Leu Phe His
                265                 270                 275

gcg agt ggt ggg aaa taggtagttt tccaggtata cctgcatggg tagtgtaaaa      925
Ala Ser Gly Gly Lys
            280

gtcgaataaa catgtcacag agtgacggac tgatataaat aaataaataa acgtgtcaca    985

gagttacata taaacaaata aataaataat taaaaatgtc cagttta                 1032


<210> SEQ ID NO 5
<211> LENGTH: 281
<212> TYPE: PRT
<213> ORGANISM: Hordeum vulgare

<400> SEQUENCE: 5

Met Ala Ala Lys Met Ala Lys Asn Val Asp Lys Pro Leu Phe Thr Ala
 1               5                  10                  15

Thr Phe Asn Val Gln Ala Ser Ser Ala Asp Tyr Ala Thr Phe Ile Ala
            20                  25                  30

Gly Ile Arg Asn Lys Leu Arg Asn Pro Ala His Phe Ser His Asn Arg
        35                  40                  45

Pro Val Leu Pro Pro Val Glu Pro Asn Val Pro Pro Ser Arg Trp Phe
    50                  55                  60

His Val Val Leu Lys Ala Ser Pro Thr Ser Ala Gly Leu Thr Leu Ala
65                  70                  75                  80

Ile Arg Ala Asp Asn Ile Tyr Leu Glu Gly Phe Lys Ser Ser Asp Gly
                85                  90                  95

Thr Trp Trp Glu Leu Thr Pro Gly Leu Ile Pro Gly Ala Thr Tyr Val
            100                 105                 110

Gly Phe Gly Gly Thr Tyr Arg Asp Leu Leu Gly Asp Thr Asp Lys Leu
        115                 120                 125

Thr Asn Val Ala Leu Gly Arg Gln Gln Leu Ala Asp Ala Val Thr Ala
    130                 135                 140

Leu His Gly Arg Thr Lys Ala Asp Lys Pro Ser Gly Pro Lys Gln Gln
145                 150                 155                 160

Gln Ala Arg Glu Ala Val Thr Thr Leu Leu Leu Met Val Asn Glu Ala
                165                 170                 175
```

-continued

```
Thr Arg Phe Gln Thr Val Ser Gly Phe Val Ala Gly Leu Leu His Pro
            180                 185                 190

Lys Ala Val Glu Lys Lys Ser Gly Lys Ile Gly Asn Glu Met Lys Ala
        195                 200                 205

Gln Val Asn Gly Trp Gln Asp Leu Ser Ala Ala Leu Leu Lys Thr Asp
    210                 215                 220

Val Lys Pro Pro Pro Gly Lys Ser Pro Ala Lys Phe Ala Pro Ile Glu
225                 230                 235                 240

Lys Met Gly Val Arg Thr Ala Val Gln Ala Ala Asn Thr Leu Gly Ile
                245                 250                 255

Leu Leu Phe Val Glu Val Pro Gly Gly Leu Thr Val Ala Lys Ala Leu
            260                 265                 270

Glu Leu Phe His Ala Ser Gly Gly Lys
        275                 280


<210> SEQ ID NO 6
<211> LENGTH: 480
<212> TYPE: DNA
<213> ORGANISM: Hordeum vulgare
<220> FEATURE:
<221> NAME/KEY: CDS
<222> LOCATION: (1)...(351)
<223> OTHER INFORMATION: protein syntheis inhibitor (PSI),
      aminoterminally incomplete protein from an incomplete PSI cDNA
      clone
<220> FEATURE:
<221> NAME/KEY: 3'UTR
<222> LOCATION: (352)...(487)
<220> FEATURE:
<221> NAME/KEY: polyA_signal
<222> LOCATION: (404)...(409)
<223> OTHER INFORMATION: potential polyadenylation signal
<220> FEATURE:
<221> NAME/KEY: polyA_signal
<222> LOCATION: (437)...(442)
<223> OTHER INFORMATION: potential polyadenylation signal
<220> FEATURE:
<221> NAME/KEY: polyA_signal
<222> LOCATION: (445)...(450)
<223> OTHER INFORMATION: potential polyadenylation signal

<400> SEQUENCE: 6

gcg gtg acg acg ctg ctc ctc atg gtg aac gag gcc acg cgg ttc cag       48
Ala Val Thr Thr Leu Leu Leu Met Val Asn Glu Ala Thr Arg Phe Gln
 1               5                  10                  15

acg gtg tcg ggg ttc gtg gcc ggg ctg ctg cac ccc aag gcg gtg gag       96
Thr Val Ser Gly Phe Val Ala Gly Leu Leu His Pro Lys Ala Val Glu
            20                  25                  30

aag aag agc ggg aag atc ggc aat gag atg aag gcc cag gtg aac ggg      144
Lys Lys Ser Gly Lys Ile Gly Asn Glu Met Lys Ala Gln Val Asn Gly
        35                  40                  45

tgg cag gac ctg tcc gcg gcg ctg ctg aag acg gac gtg aag ccc ccg      192
Trp Gln Asp Leu Ser Ala Ala Leu Leu Lys Thr Asp Val Lys Pro Pro
    50                  55                  60

ccg gga aag tcg cca gcg aag ttc acg ccg atc gag aag atg ggc gtg      240
Pro Gly Lys Ser Pro Ala Lys Phe Thr Pro Ile Glu Lys Met Gly Val
65                  70                  75                  80

agg act gct gag cag gct gcg gct act ttg ggg atc ctg ctg ttc gtt      288
Arg Thr Ala Glu Gln Ala Ala Ala Thr Leu Gly Ile Leu Leu Phe Val
                85                  90                  95

gag gtg ccg ggt ggg ttg acg gtg gcc aag gcg ctg gag ctg ttt cat      336
Glu Val Pro Gly Gly Leu Thr Val Ala Lys Ala Leu Glu Leu Phe His
            100                 105                 110

gcg agt ggt ggg aaa taggtagttt tgcaggtata cctgcatggg taaatgtaaa      391
```

-continued

```
Ala Ser Gly Gly Lys
        115

agtcgaataa aaatgtcaca gagtgacgga ctgatataaa taaattaata aacatgtcat    451

catgagtgac agactgatat aaataaata                                      480


<210> SEQ ID NO 7
<211> LENGTH: 117
<212> TYPE: PRT
<213> ORGANISM: Hordeum vulgare

<400> SEQUENCE: 7

Ala Val Thr Thr Leu Leu Leu Met Val Asn Glu Ala Thr Arg Phe Gln
 1               5                  10                  15

Thr Val Ser Gly Phe Val Ala Gly Leu Leu His Pro Lys Ala Val Glu
            20                  25                  30

Lys Lys Ser Gly Lys Ile Gly Asn Glu Met Lys Ala Gln Val Asn Gly
        35                  40                  45

Trp Gln Asp Leu Ser Ala Ala Leu Leu Lys Thr Asp Val Lys Pro Pro
    50                  55                  60

Pro Gly Lys Ser Pro Ala Lys Phe Thr Pro Ile Glu Lys Met Gly Val
65                  70                  75                  80

Arg Thr Ala Glu Gln Ala Ala Ala Thr Leu Gly Ile Leu Leu Phe Val
                85                  90                  95

Glu Val Pro Gly Gly Leu Thr Val Ala Lys Ala Leu Glu Leu Phe His
            100                 105                 110

Ala Ser Gly Gly Lys
        115


<210> SEQ ID NO 8
<211> LENGTH: 2329
<212> TYPE: DNA
<213> ORGANISM: Serratia marcescens
<220> FEATURE:
<221> NAME/KEY: misc_feature
<222> LOCATION: (1)...(2329)
<223> OTHER INFORMATION: ChiS gene from plasmid pLChis from E.coli A5187

<400> SEQUENCE: 8

cagggcgttg tcaataatga caacaccctg gctgaagagt gtggtgcaat actgataaat     60

atttatcttt ccttaataga aaattcacta tccttatttg tcatgttttc ttttatttat    120

atgaaaataa attcacgctt gctgaataaa acccagttga tagcgctctt gtttttgcgc    180

ctttttttatt tatagtactg aatgtacgcg gtgggaatga ttatttcgcc acgtggaaag    240

acgctgttgt tatttattga ttttaacctt cgcggattat tgcggaattt tttcgcttcg    300

gcaatgcatc gcgacgatta actcttttat gtttatcctc tcggaataaa ggaatcagtt    360

atgcgcaaat ttaataaacc gctgttggcg ctgttgatcg gcagcacgct gtgttccgcg    420

gcgcaggccg ccgcgccggg caagccgacc atcgcctggg gcaacaccaa gttcgccatc    480

gttgaagttg accaggcggc taccgcttat aataatttgg tgaaggtaaa aaatgccgcc    540

gatgtttccg tctcctggaa tttatggaat ggcgacaccg gcacgacggc aaaagtttta    600

ttaaatggca aagaggcgtg gagtggtcct tcaaccggat cttccggtac ggcgaatttt    660

aaagtgaata aaggcggccg ttatcaaatg caggtggcac tgtgcaatgc cgacggctgc    720

accgccagtg acgccaccga aattgtggta gccgacaccg acggcagcca tttggcgccg    780

ttgaaagagc cgctgctgga aaagaataaa ccgtataaac agaactccgg caaagtggtc    840
```

-continued

```
ggttcttatt tcgtcgagtg gggcgtttac gggcgcaatt tcaccgtcga caagatcccg    900
gcgcaaaacc tgacccacct gctgtacggc tttatcccga tctgcggcgg caatggcatc    960
aacgacagcc tgaaagagat tgaaggcagc ttccaggcgt tgcagcgctc ctgccagggc   1020
cgcgaggact tcaaagtctc gatccacgat ccgttcgccc cgctgcaaaa agcgcagaag   1080
ggcgtgaccg cctgggatga cccctacaag ggcaacttcg gccagctgat ggcgctgaag   1140
caggcgcatc ctgacctgaa aatcctgccg tcgatcggcg gctggacgct gtccgacccg   1200
ttcttcttca tgggcgacaa ggtgaagcgc gatcgcttcg tcggttcggt gaaagagttc   1260
ctgcagacct ggaagttctt cgacggcgtg gatatcgact gggagttccc gggcggcaaa   1320
ggcgccaacc ctaacctggg cagcccgcaa gacggggaaa cctatgtgct gctgatgaag   1380
gagctgcggg cgatgctgga tcagctgtcg gtggaaaccg gccgcaagta tgagctgacc   1440
tccgccatca gcgccggtaa ggacaagatc gacaaggtgg cttacaacgt tgcgcagaac   1500
tcgatggatc acatcttcct gatgagctac gacttctatg gcgccttcga tctgaagaac   1560
ctggggcatc agaccgcgct gaatgcgccg gcctggaaac cggacaccgc ctacaccacg   1620
gtgaacggcg tcaatgcgct gctggcgcag ggcgtcaagc cgggcaaaat cgtcgtcggc   1680
accgccatgt atggccgcgg ctggaccggg gtgaacggct accagaacaa tattccgttc   1740
accggcaccg ccaccgggcc ggttaaaggc acctgggaga acggtatcgt ggactaccgc   1800
caaatcgccg gccagttcat gagcggcgag tggcagtata cctacgacgc cacggcggaa   1860
gcgccttacg tgttcaaacc ttccaccggc gatctgatca ccttcgacga tgcccgctcg   1920
gtgcaggcta aaggcaagta cgtgttggat aagcagctgg gcggcctgtt ctcctgggag   1980
atcgacgcgg ataacggcga tattctcaac agcatgaacg ccagcctggg caacagcgcc   2040
ggcgttcaat aatcggttgc agtggttgcc gggggatatc ctttcgcccc cggctttttc   2100
gccgacgaaa gtttttttac gccgcacaga ttgtggctct gccccgagca aaacgcgctc   2160
atcggactca ccctttttggg taatccttca gcatttcctc ctgtctttaa cggcgatcac   2220
aaaaataacc gttcagatat tcatcattca gcaacaaagt tttggcgttt tttaacggag   2280
ttaaaaacca gtaagtttgt gagggtcaga ccaatgcgct aaaaatggg               2329
```

```
<210> SEQ ID NO 9
<211> LENGTH: 1002
<212> TYPE: DNA
<213> ORGANISM: Hordeum vulgare
<220> FEATURE:
<221> NAME/KEY: 5'UTR
<222> LOCATION: (1)...(63)
<220> FEATURE:
<221> NAME/KEY: CDS
<222> LOCATION: (64)...(861)
<223> OTHER INFORMATION: 26 kD preprotein of chitinase (ChiG)
<220> FEATURE:
<221> NAME/KEY: 3'UTR
<222> LOCATION: (862)...(1002)
<223> OTHER INFORMATION: partial, 11 nucleotides at 3' end not shown
<220> FEATURE:
<221> NAME/KEY: polyA_signal
<222> LOCATION: (905)...(910)
<223> OTHER INFORMATION: potential polyadenylation site
<220> FEATURE:
<221> NAME/KEY: sig_peptide
<222> LOCATION: (64)...(294)
<223> OTHER INFORMATION: probable signal peptide
<220> FEATURE:
<221> NAME/KEY: sig_peptide
<222> LOCATION: (298)...(312)
<223> OTHER INFORMATION: probable signal peptide
<220> FEATURE:
```

-continued

```
<221> NAME/KEY: sig_peptide
<222> LOCATION: (349)...(378)
<223> OTHER INFORMATION: probable signal peptide
<220> FEATURE:
<221> NAME/KEY: sig_peptide
<222> LOCATION: (466)...(588)
<223> OTHER INFORMATION: probable signal peptide
<220> FEATURE:
<221> NAME/KEY: sig_peptide
<222> LOCATION: (607)...(861)
<223> OTHER INFORMATION: probable signal peptide
<220> FEATURE:
<221> NAME/KEY: mat_peptide
<222> LOCATION: (133)...(861)

<400> SEQUENCE: 9

cctacgacag tagcgtaacg gtaaacaccg agtacggtac tctgtgcttt gttggctcgc     60

aca atg aga tcg ctc gcg gtg gtg gtg gcc gtg gta gcc acg gtg gcc      108
    Met Arg Ser Leu Ala Val Val Val Ala Val Val Ala Thr Val Ala
     1               5                  10                  15

atg gcc atc ggc acg gcg cgc ggc agc gtg tcc tcc atc gtc tcg cgc      156
Met Ala Ile Gly Thr Ala Arg Gly Ser Val Ser Ser Ile Val Ser Arg
                20                  25                  30

gca cag ttt gac cgc atg ctt ctc cac cgc aac gac ggc gcc tgc cag      204
Ala Gln Phe Asp Arg Met Leu Leu His Arg Asn Asp Gly Ala Cys Gln
            35                  40                  45

gcc aag ggc ttc tac acc tac gac gcc ttc gtc gcc gcc gca gcc gcc      252
Ala Lys Gly Phe Tyr Thr Tyr Asp Ala Phe Val Ala Ala Ala Ala Ala
        50                  55                  60

ttc ccg ggc ttc ggc acc acc ggc agc gcc gac gcc cag aag cgc gag      300
Phe Pro Gly Phe Gly Thr Thr Gly Ser Ala Asp Ala Gln Lys Arg Glu
    65                  70                  75

gtg gcc gcc ttc cta gca cag acc tcc cac gag acc acc ggc ggg tgg      348
Val Ala Ala Phe Leu Ala Gln Thr Ser His Glu Thr Thr Gly Gly Trp
80                  85                  90                  95

gcg act gca ccg gac ggg gcc ttc gcc tgg ggc tac tgc ttc aag cag      396
Ala Thr Ala Pro Asp Gly Ala Phe Ala Trp Gly Tyr Cys Phe Lys Gln
                100                 105                 110

gaa cgt ggc gcc tcc tcc gac tac tgc acc ccg agc gca caa tgg ccg      444
Glu Arg Gly Ala Ser Ser Asp Tyr Cys Thr Pro Ser Ala Gln Trp Pro
            115                 120                 125

tgc gcc ccc ggg aag cgc tac tac ggc cgc ggg cca atc cag ctc tcc      492
Cys Ala Pro Gly Lys Arg Tyr Tyr Gly Arg Gly Pro Ile Gln Leu Ser
        130                 135                 140

cac aac tac aac tat gga cct gcc ggc cgg gcc atc ggg gtc gat ctg      540
His Asn Tyr Asn Tyr Gly Pro Ala Gly Arg Ala Ile Gly Val Asp Leu
    145                 150                 155

ctg gcc aac ccg gac ctg gtg gcc acg gac gcc act gtg ggc ttt aag      588
Leu Ala Asn Pro Asp Leu Val Ala Thr Asp Ala Thr Val Gly Phe Lys
160                 165                 170                 175

acg gcc atc tgg ttc tgg atg acg gcg cag ccg ccc aag cca tcg agc      636
Thr Ala Ile Trp Phe Trp Met Thr Ala Gln Pro Pro Lys Pro Ser Ser
                180                 185                 190

cat gct gtg atc gcc ggc cag tgg agc ccg tca ggg gct gac cgg gcc      684
His Ala Val Ile Ala Gly Gln Trp Ser Pro Ser Gly Ala Asp Arg Ala
            195                 200                 205

gca ggc cgg gtg ccc ggg ttt ggt gtg atc acc aac atc atc aac ggc      732
Ala Gly Arg Val Pro Gly Phe Gly Val Ile Thr Asn Ile Ile Asn Gly
        210                 215                 220

ggg atc gag tgc ggt cac ggg cag gac agc cgc gtc gcc gat cga atc      780
Gly Ile Glu Cys Gly His Gly Gln Asp Ser Arg Val Ala Asp Arg Ile
    225                 230                 235
```

-continued

```
ggg ttt tac aag cgc tac tgt gac atc ctc ggc gtt ggc tac ggc aac      828
Gly Phe Tyr Lys Arg Tyr Cys Asp Ile Leu Gly Val Gly Tyr Gly Asn
240                 245                 250                 255

aac ctc gat tgc tac agc cag aga ccc ttc gcc taattaatta gtcatgtatt    881
Asn Leu Asp Cys Tyr Ser Gln Arg Pro Phe Ala
                260                 265

aatcttggcc ctccataaaa tacaataaga gcatcgtctc ctatctacat gctgtaagat    941

gtaactatgg taacctttta tggggaacat aacaaaggca tctcgtatag atgctttgct   1001

a                                                                   1002


<210> SEQ ID NO 10
<211> LENGTH: 266
<212> TYPE: PRT
<213> ORGANISM: Hordeum vulgare

<400> SEQUENCE: 10

Met Arg Ser Leu Ala Val Val Val Ala Val Val Ala Thr Val Ala Met
 1               5                  10                  15

Ala Ile Gly Thr Ala Arg Gly Ser Val Ser Ser Ile Val Ser Arg Ala
            20                  25                  30

Gln Phe Asp Arg Met Leu Leu His Arg Asn Asp Gly Ala Cys Gln Ala
        35                  40                  45

Lys Gly Phe Tyr Thr Tyr Asp Ala Phe Val Ala Ala Ala Ala Ala Phe
    50                  55                  60

Pro Gly Phe Gly Thr Thr Gly Ser Ala Asp Ala Gln Lys Arg Glu Val
65                  70                  75                  80

Ala Ala Phe Leu Ala Gln Thr Ser His Glu Thr Thr Gly Gly Trp Ala
                85                  90                  95

Thr Ala Pro Asp Gly Ala Phe Ala Trp Gly Tyr Cys Phe Lys Gln Glu
            100                 105                 110

Arg Gly Ala Ser Ser Asp Tyr Cys Thr Pro Ser Ala Gln Trp Pro Cys
        115                 120                 125

Ala Pro Gly Lys Arg Tyr Tyr Gly Arg Gly Pro Ile Gln Leu Ser His
    130                 135                 140

Asn Tyr Asn Tyr Gly Pro Ala Gly Arg Ala Ile Gly Val Asp Leu Leu
145                 150                 155                 160

Ala Asn Pro Asp Leu Val Ala Thr Asp Ala Thr Val Gly Phe Lys Thr
                165                 170                 175

Ala Ile Trp Phe Trp Met Thr Ala Gln Pro Pro Lys Pro Ser Ser His
            180                 185                 190

Ala Val Ile Ala Gly Gln Trp Ser Pro Ser Gly Ala Asp Arg Ala Ala
        195                 200                 205

Gly Arg Val Pro Gly Phe Gly Val Ile Thr Asn Ile Ile Asn Gly Gly
    210                 215                 220

Ile Glu Cys Gly His Gly Gln Asp Ser Arg Val Ala Asp Arg Ile Gly
225                 230                 235                 240

Phe Tyr Lys Arg Tyr Cys Asp Ile Leu Gly Val Gly Tyr Gly Asn Asn
                245                 250                 255

Leu Asp Cys Tyr Ser Gln Arg Pro Phe Ala
            260                 265


<210> SEQ ID NO 11
<211> LENGTH: 1235
<212> TYPE: DNA
<213> ORGANISM: Hordeum vulgare
```

-continued

```
<220> FEATURE:
<221> NAME/KEY: 5'UTR
<222> LOCATION: (1)...(48)
<220> FEATURE:
<221> NAME/KEY: CDS
<222> LOCATION: (49)...(1050)
<223> OTHER INFORMATION: preprotein of the glucanase GluG
<220> FEATURE:
<221> NAME/KEY: 3'UTR
<222> LOCATION: (1051)...(1235)
<223> OTHER INFORMATION: partial, 14 nucleotides at the 3' end not shown
<220> FEATURE:
<221> NAME/KEY: polyA_signal
<222> LOCATION: (1083)...(1088)
<223> OTHER INFORMATION: potential polyadenylation signal
<220> FEATURE:
<221> NAME/KEY: polyA_signal
<222> LOCATION: (1210)...(1215)
<223> OTHER INFORMATION: potential polyadenylation signal
<220> FEATURE:
<221> NAME/KEY: mat_peptide
<222> LOCATION: (133)...(1050)

<400> SEQUENCE: 11

ggcagcattg catagcattt gagcaccaga tactccgtgt gtgcacca atg gct aga      57
                                                     Met Ala Arg
                                                      1

aaa gat gtt gcc tcc atg ttt gca gtt gct ctc ttc att gga gca ttc      105
Lys Asp Val Ala Ser Met Phe Ala Val Ala Leu Phe Ile Gly Ala Phe
     5                  10                  15

gct gct gtt cct acg agt gtg cag tcc atc ggc gta tgc tac ggc gtg      153
Ala Ala Val Pro Thr Ser Val Gln Ser Ile Gly Val Cys Tyr Gly Val
 20                  25                  30                  35

atc ggc aac aac ctc ccc tcc cgg agc gac gtg gtg cag ctc tac agg      201
Ile Gly Asn Asn Leu Pro Ser Arg Ser Asp Val Val Gln Leu Tyr Arg
                 40                  45                  50

tcc aag ggc atc aac ggc atg cgc atc tac ttc gcc gac ggg cag gcc      249
Ser Lys Gly Ile Asn Gly Met Arg Ile Tyr Phe Ala Asp Gly Gln Ala
             55                  60                  65

ctc tcg gcc gtc cgc aac tcc ggc atc ggc ctc atc ctc gac atc ggc      297
Leu Ser Ala Val Arg Asn Ser Gly Ile Gly Leu Ile Leu Asp Ile Gly
         70                  75                  80

aac gac cag ctc gcc aac atc gcc gcc agc acc tcc aac gcg gcc tcc      345
Asn Asp Gln Leu Ala Asn Ile Ala Ala Ser Thr Ser Asn Ala Ala Ser
     85                  90                  95

tgg gtc cag aac aac gtg cgg ccc tac tac cct gcc gtg aac atc aag      393
Trp Val Gln Asn Asn Val Arg Pro Tyr Tyr Pro Ala Val Asn Ile Lys
100                 105                 110                 115

tac atc gcc gcc ggc aac gag gtg cag ggc ggc gcc acg cag agc atc      441
Tyr Ile Ala Ala Gly Asn Glu Val Gln Gly Gly Ala Thr Gln Ser Ile
                120                 125                 130

ctg ccg gcc atg cgc aac ctc aac gcg gcc ctc tcc gcg gcg ggg ctc      489
Leu Pro Ala Met Arg Asn Leu Asn Ala Ala Leu Ser Ala Ala Gly Leu
            135                 140                 145

ggc gcc atc aag gtg tcc acc tcc atc cgg ttc gac gag gtg gcc aac      537
Gly Ala Ile Lys Val Ser Thr Ser Ile Arg Phe Asp Glu Val Ala Asn
        150                 155                 160

tcc ttc ccg ccc tcc gcc ggc gtg ttc aag aac gcc tac atg acg gac      585
Ser Phe Pro Pro Ser Ala Gly Val Phe Lys Asn Ala Tyr Met Thr Asp
    165                 170                 175

gtg gcc cgg ctc ctg gcg agc acc ggc gcg ccg ctg ctc gcc aac gtc      633
Val Ala Arg Leu Leu Ala Ser Thr Gly Ala Pro Leu Leu Ala Asn Val
180                 185                 190                 195

tac ccc tac ttc gcg tac cgt gac aac ccc ggg agc atc agc ctg aac      681
Tyr Pro Tyr Phe Ala Tyr Arg Asp Asn Pro Gly Ser Ile Ser Leu Asn
```

-continued

```
                200                 205                 210

tac gcg acg ttc cag ccg ggc acc acc gtg cgt gac cag aac aac ggg      729
Tyr Ala Thr Phe Gln Pro Gly Thr Thr Val Arg Asp Gln Asn Asn Gly
            215                 220                 225

ctg acc tac acg tcc ctg ttc gac gcg atg gtg gac gcc gtg tac gcg      777
Leu Thr Tyr Thr Ser Leu Phe Asp Ala Met Val Asp Ala Val Tyr Ala
        230                 235                 240

gcg ctg gag aag gcc ggc gcg ccg gcg gtg aag gtg gtg gtg tcg gag      825
Ala Leu Glu Lys Ala Gly Ala Pro Ala Val Lys Val Val Val Ser Glu
    245                 250                 255

agc ggg tgg ccg tcg gcg ggc ggg ttt gcg gcg tcg gcc ggc aat gcg      873
Ser Gly Trp Pro Ser Ala Gly Gly Phe Ala Ala Ser Ala Gly Asn Ala
260                 265                 270                 275

cgg acg tac aac cag ggg ctg atc aac cac gtc ggc ggg ggc acg ccc      921
Arg Thr Tyr Asn Gln Gly Leu Ile Asn His Val Gly Gly Gly Thr Pro
                280                 285                 290

aag aag cgg gag gcg ctg gag acg tac atc ttc gcc atg ttc aac gag      969
Lys Lys Arg Glu Ala Leu Glu Thr Tyr Ile Phe Ala Met Phe Asn Glu
            295                 300                 305

aac cag aag acc ggg gac gcc acg gag agg agc ttc ggg ctc ttc aac     1017
Asn Gln Lys Thr Gly Asp Ala Thr Glu Arg Ser Phe Gly Leu Phe Asn
        310                 315                 320

ccg gac aag tcg ccg gca tac aac atc cag ttc tagtacgtgt agctacctag   1070
Pro Asp Lys Ser Pro Ala Tyr Asn Ile Gln Phe
    325                 330

ctcacatacc taaataaata agctgcacgt acgtacgtaa tgcggcatcc aagtgtaacg   1130

tagacacgta cattcatcca tggaagagtg caaccaagca tgcgttaact tcctggtgat   1190

gatacatcat catggtatga ataaaagata tggaagatgt tatga                   1235


<210> SEQ ID NO 12
<211> LENGTH: 334
<212> TYPE: PRT
<213> ORGANISM: Hordeum vulgare

<400> SEQUENCE: 12

Met Ala Arg Lys Asp Val Ala Ser Met Phe Ala Val Ala Leu Phe Ile
 1               5                  10                  15

Gly Ala Phe Ala Ala Val Pro Thr Ser Val Gln Ser Ile Gly Val Cys
            20                  25                  30

Tyr Gly Val Ile Gly Asn Asn Leu Pro Ser Arg Ser Asp Val Val Gln
        35                  40                  45

Leu Tyr Arg Ser Lys Gly Ile Asn Gly Met Arg Ile Tyr Phe Ala Asp
    50                  55                  60

Gly Gln Ala Leu Ser Ala Val Arg Asn Ser Gly Ile Gly Leu Ile Leu
65                  70                  75                  80

Asp Ile Gly Asn Asp Gln Leu Ala Asn Ile Ala Ala Ser Thr Ser Asn
                85                  90                  95

Ala Ala Ser Trp Val Gln Asn Asn Val Arg Pro Tyr Tyr Pro Ala Val
            100                 105                 110

Asn Ile Lys Tyr Ile Ala Ala Gly Asn Glu Val Gln Gly Gly Ala Thr
        115                 120                 125

Gln Ser Ile Leu Pro Ala Met Arg Asn Leu Asn Ala Ala Leu Ser Ala
    130                 135                 140

Ala Gly Leu Gly Ala Ile Lys Val Ser Thr Ser Ile Arg Phe Asp Glu
145                 150                 155                 160

Val Ala Asn Ser Phe Pro Pro Ser Ala Gly Val Phe Lys Asn Ala Tyr
```

-continued

```
                165                 170                 175

Met Thr Asp Val Ala Arg Leu Leu Ala Ser Thr Gly Ala Pro Leu Leu
            180                 185                 190

Ala Asn Val Tyr Pro Tyr Phe Ala Tyr Arg Asp Asn Pro Gly Ser Ile
        195                 200                 205

Ser Leu Asn Tyr Ala Thr Phe Gln Pro Gly Thr Thr Val Arg Asp Gln
    210                 215                 220

Asn Asn Gly Leu Thr Tyr Thr Ser Leu Phe Asp Ala Met Val Asp Ala
225                 230                 235                 240

Val Tyr Ala Ala Leu Glu Lys Ala Gly Ala Pro Ala Val Lys Val Val
                245                 250                 255

Val Ser Glu Ser Gly Trp Pro Ser Ala Gly Gly Phe Ala Ala Ser Ala
            260                 265                 270

Gly Asn Ala Arg Thr Tyr Asn Gln Gly Leu Ile Asn His Val Gly Gly
        275                 280                 285

Gly Thr Pro Lys Lys Arg Glu Ala Leu Glu Thr Tyr Ile Phe Ala Met
    290                 295                 300

Phe Asn Glu Asn Gln Lys Thr Gly Asp Ala Thr Glu Arg Ser Phe Gly
305                 310                 315                 320

Leu Phe Asn Pro Asp Lys Ser Pro Ala Tyr Asn Ile Gln Phe
                325                 330
```

We claim:

1. A process for producing a plant having increased resistance to fungal attack, comprising topically applying, to a transgenic plant, a first gene product of a gene selected from the group consisting of a ChiG gene from barley, a GluG gene from barley, a PSI gene from barley, and an AFP gene from Aspergillus giganteus, wherein the transgenic plant carries at least two transgenes, each operably linked to a plant-functional promoter, wherein one transgene is a ChiS gene from Serratia marcescens and a second transgene is a gene selected from the group consisting of a ChiG gene from barley, a GluG gene from barley, a PSI gene from barley, and an AFP gene from Aspergillus giganteus, provided that the second transgene does not encode the first gene product.

2. A process for producing a plant having increased resistance to fungal attack, comprising topically applying, to a transgenic plant, a first gene product of a gene selected from the group consisting of a ChiG gene from barley, a GluG gene from barley, a PSI gene from barley, and a ChiS gene from Serratia marcescens, wherein the transgenic plant carries at least two transgenes, each operably linked to a plant-functional promoter, wherein one transgene is an AFP gene from Aspergillus giganteus and a second transgene is a gene selected from the group consisting of a ChiG gene from barley, a GluG gene from barley, a PSI gene from barley, and a ChiS gene from Serratia marcescens, provided that the second transgene does not encode the first gene product.

* * * * *